United States Patent [19]

Milstein et al.

[11] 4,044,064

[45] Aug. 23, 1977

[54] CONVERSION OF FISCHER-TROPSCH HEAVY PRODUCT TO HIGH QUALITY JET FUEL

[75] Inventors: Donald Milstein; Thomas R. Stein, both of Cherry Hill, N.J.

[73] Assignee: Mobil Oil Corporation, New York, N.Y.

[21] Appl. No.: 671,511

[22] Filed: Mar. 29, 1976

[51] Int. Cl.[2] .................................... C07C 1/04

[52] U.S. Cl. .................................... 260/676 R; 208/79; 208/88; 208/93; 208/120; 208/135; 260/449R; 260/450

[58] Field of Search .......... 260/676 R, 449 R, 449 M, 260/449.5, 449.6, 450; 208/57, 64, 79, 88, 93

[56] References Cited

U.S. PATENT DOCUMENTS

| | | | |
|---|---|---|---|
| 2,740,804 | 4/1956 | Glazier | 260/450 |
| 2,752,382 | 6/1956 | Garrett et al. | 260/450 |
| 3,172,842 | 3/1965 | Paterson | 208/79 |
| 3,700,585 | 10/1972 | Chen et al. | 208/111 |
| 3,729,409 | 4/1973 | Chen | 208/135 |
| 3,760,024 | 9/1973 | Cattanach | 260/673 |
| 3,843,510 | 10/1974 | Morrison et al. | 208/111 |
| 3,928,483 | 12/1975 | Chang et al. | 260/668 R |
| 3,960,978 | 6/1976 | Givens | 260/683.15 R |

OTHER PUBLICATIONS

Asinger, Paraffins Chemistry & Technology, Pergamon Press, N.Y. (1968) pp. 3, 123–125, 131, 132, 136, 138.

*Primary Examiner*—C. Davis
*Attorney, Agent, or Firm*—Charles A. Huggett; Carl D. Farnsworth

[57] ABSTRACT

Upgrading a fraction of a heavy Fischer-Tropsch oil to jet fuel by hydropretreating a 350° to 850° F boiling fraction; separating the hydrotreated product into a 650° F minus and a 650° F plus fraction, separating the650° F minus fraction to provide a 350° F minus naphtha boiling range fraction and a 350° to 650° F light distillate fraction; distilling the 350° to 650° F hydrotreated fraction to provide a fraction boiling in the range of 350° F to 550° F separate from a 550° to 650° F fraction processing either of the 650° F plus fraction above separated or the 350° to 550° F boiling fraction above obtained over a catalyst comprising a crystalline aluminosilicate zeolite having a silica to alumina ratio of at least 12 and a constraint index of 1 to 12 with hydrogen, at a temperature of about 500° to 800° F, a hydrogen partial pressure of about 100 to 800 psig and a space velocity in the range of about 0.5 to 5 LHSV to produce a converted product comprising lower boiling hydrocarbons than the feed charged and recovering as a product of the process a reduced pour point diesel oil fraction, a 350° to 550° F jet fuel fraction, and a 350° F minus naphtha product fraction.

9 Claims, 1 Drawing Figure

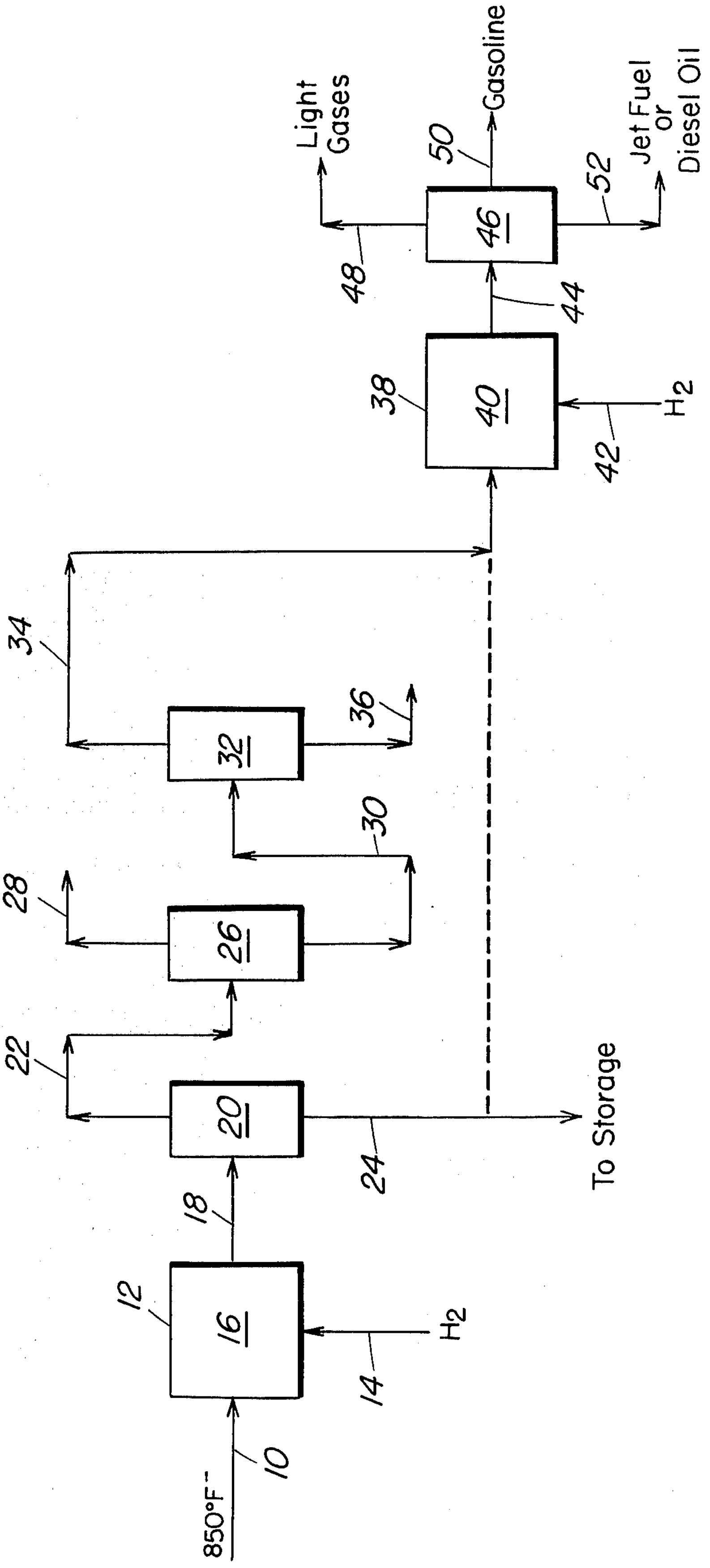
Light Gases
Gasoline
Jet Fuel or Diesel Oil
50
52
48
46
44
38
40
$H_2$
42
34
36
32
30
28
26
22
20
24
To Storage
18
12
16
$H_2$
14
10
850°F$^{-}$

CONVERSION OF FISCHER-TROPSCH HEAVY PRODUCT TO HIGH QUALITY JET FUEL

This invention relates to the upgrading of synthetic hydrocarbon streams. It more particularly refers to a method and process arrangement for upgrading a synthetic fraction of Fischer-Tropsch synthesis comprising hydrocarbons and oxygenates boiling above about 350° F into a product slate including high quality jet fuel.

It is known that jet fuel must have a rather low freeze point because it must be a pumpable fluid at high altitudes where the low temperatures are almost always encountered. A known technique for providing jet fuel is to take a light kerosine (350° to 450° F) fraction from crude petroleum and adjust its freeze point and smoke point by conventional techniques including solvent extraction and/or dewaxing. It has also been proposed to adjust the pour point, cloud point and/or freeze point of a hydrocarbon distillate fraction, including kerosines by selective catalytic conversion of the feed.

One such catalytic conversion utilizes catalysts comprising ZSM-5 and/or similarly behaving crystalline aluminosilicate zeolites. These catalytic materials have high silica to alumina ratios of greater than 12, contraint indices (as defined in U.S. Pat. No. 3,894,102) of 1 to 12 and preferably a crystal density of not substantially below about 1.6 grams per cubic centimeter. Other zeolites which conform to these parameters are ZSM-11, ZSM-12, ZSM-35, and ZSM-38. This catalytic conversion is suitably operated at a temperature in the range of about 500° to 800° F. In a preferred operation, the catalyst has a hydrogenation/dehydrogenation component incorporated therewith, such as nickel, and the conversion is maintained under some hydrogen pressure. This preferred operation lengthens the catalyst cycle life and therefore contributes to the economy of the operation.

In recent times, there has been a renewed interest in the production of hydrocarbon products from coal. One such technique utilizes the known Fischer-Tropsch Synthesis process for converting synthesis gas (CO and $H_2$) to a hydrocarbon product varying considerably in boiling range and comprising oxygenates and waxy material boiling above about 650° F that does not contain the sulfur, nitrogen or metal impurities often found in crude oil. The Fischer-Tropsch hydrocarbon product is roughly separated initially by successive cooling operations, usually by indirect cooling, to first separate out a relatively heavy fraction of hydrocarbons and oxygenates boiling above about 350° or 400° F from lower boiling material comprising gasoline range material. The material boiling above 400° F is known as decant oil. The synthetic product boiling below 400° F is further cooled to isolate a $C_5$ to 400° F gasoline boiling range material from lower boiling gaseous materials.

The Fischer-Tropsch product boiling above 350° or 400° F is highly aliphatic and in fact is highly definic with normal 1-olefins predominating. It is a difficult material to convert to reasonable quality distillate products, particularly to high quality jet fuel.

It is, therefore, an object of this invention to provide a process for upgrading a Fischer-Tropsch product boiling above 350° F comprising oxygenates to produce quality distillate products including a high quality jet fuel.

Other and additional objects of this invention will become more apparent from a consideration of this entire specification including the drawing and the claims hereof.

Understanding of this invention will be facilitated by reference to the accompanying drawing, the single Figure of which is a block flow diagram of the preferred aspect of the process of this invention.

In accord with and fulfilling these objects, one aspect of this invention resides in upgrading a Fischer-Tropsch decant oil by the following sequence of process steps. In this specific process description, the decant oil being upgraded has a boiling range of about 350° to 850° F. Decant oils of other or more narrow boiling ranges may also be upgraded by the process of this invention but the boiling range specified will be used for illustrative purposes as being representative and convenient.

The decant oil is first subjected to a hydropretreatment or hydrogenation operation under conditions sufficiently severe to saturate olefins and remove oxygenates, particulary organic acids. This treatment causes some general reduction in molecular weight and boiling range. The hydrotreated product is separated to provide an overhead fraction which roughly boils below about 650° F. The bottoms product obtained from the separation is roughly a 650° F plus material. The overhead or 650° minus fraction is then distilled to remove naphtha with a 350° to 400° F end boiling point from a bottoms fraction comprising an initial boiling point, 350° to 400° F. The bottoms or high boiling material recovered from this naphtha distillation step and comprising 350° to 400° F initial boiling point material is thereafter separated into a ligh kerosine fraction boiling up to about 550° F of unacceptable freeze point and a 550° to 650° F diesel oil fraction having in general an acceptable pour and cloud point.

In the combination process of this invention, crystalline zeolite catalytic upgrading with hydrogen of a portion of the hydrogenated feed is accomplished by contact with a special zeolite catalyst herein described. In this zeolite catalytic upgrading operation either the 650° F plus fraction alone or the separated light fraction boiling up to 550° F alone or a combination of the two streams is processed, it being preferred to use a blocked out operation and processing each fraction separately. The fraction selected to be processed is passed over a special zeolite having silica to alumina ratio of at least 12, a constraint index of 1 to 12 and preferably a crystal density of not substantially below about 1.6 grams per cubic centimeter at a temperature in the range of about 500° to 800° F at a space velocity in the range of about 0.5 to 5 LHSV and preferably under a hydrogen pressure of about 100 to 800 psig. Where the preferred hydrogen pressure operation is used, the zeolite catalyst preferably has incorporated therewith a suitable hydrogenation/dehydrogenation component, most preferably nickel, in a proportion of about 0.5 to 5 weight percent.

It is usual to carry out this zeolite catalyst conversion and upgrading operation with a fixed catalyst bed that is periodically taken out of service and regenerated. It is possible to utilize a dense fluidized catalyst bed system or even a dispersed phase fluidized or transport (FCC type) catalyst system with continuous regeneration of circulated catalyst, or at least a portion of the circulated catalyst. The product of this zeolite catalyst upgrading operation will vary with feed charged and operating conditions employed and generally is composed of light hydrocarbon gases, a relatively high quality naphtha fraction boiling below 350° or 400° F, a jet fuel fraction boiling above 350° or 400° F and having an end point in the range of 450° to 550° F; and an upgraded distillate fraction boiling above 450° F and more usually above about 550° F. The distillate fraction and the jet fuel product are particularly desired products and operating conditions are chosen along with feed boiling range charged so as to maximize the particular product desired while still meeting the product specifications, such as pour point, freeze point, etc.

The product of this zeolite catalyst upgrading operation is separated or distilled to recover a light gaseous product, a naphtha fraction, a jet fuel, and a bottoms fraction boiling above 450° F and more usually above about 550° F. When the process is particularly directed to producing jet fuel, the zeolite catalyst upgraded product is distilled to separate a 350° F minus naphtha overhead from a low freeze point 350° to 550° F jet fuel fraction. In the diesel oil maximizing operation, the zeolite catalyst upgraded product is distilled to recover a 400° minus naphtha fraction from a 400° to 850° F distillate fraction of reduced pour point and particularly suitable for use as diesel oil. In either of the referred to operations a naphtha distillate fraction can be separated and further octane improved by processing means not shown or sent directly to a gasoline pool. In the diesel oil producing operation, the distillate (pour point reduced) 400° to 850° F fraction separated from the zeolite catalyst conversion operation product may be combined with a 400° to 650° F fraction separated from the product of the hydrogenation operation to produce specification grade, wide boiling range diesel oil.

Referring now to the drawing by way of a specific operating example, a synthetic, highly olefinic full range hydrocarbon product of Fischer-Tropsch synthesis and comprising oxygenates is separated in a series of cooling steps not shown to produce light oil and decant oil boiling in the range of 350° F up to about 850° F.

The 350° F plus synthetic oil fraction comprising highly olefinic aliphatic compounds and oxygenates is introduced by conduit 10 as charge to a hydropretreater or hydrogenation zone 12 along with hydrogen in conduit 14. The hydrotreater zone 12 is provided with one of a known hydrotreating catalyst 16 such as Co/Mo on alumina in a fixed bed and maintained at a temperature in the range of about 500°–750° F; a pressure in the range of about 300°–1000 psig and a space velocity in the range of about 1–10 LHSV.

The hydropretreated product now substantially reduced or eliminated of olefins and oxygenates, and its lower boiling range materials enriched by the hydrotreating is passed by conduit 18 to a separation zone 20 wherein a separation is made to provide a 650° F minus fraction withdrawn overhead by conduit 22 and a 650° F plus fraction withdrawn as a bottoms fraction by conduit 24. This 650° F plus bottoms fraction in conduit 24 may be passed to storage (not shown) or in one embodiment of this process, it is further processed as will be described below. The 650° F minus fraction in conduit 22 is further separated in zone 26 to provide a 350° F minus naphtha fraction withdrawn therefrom by conduit 28 and a 350° F plus fraction recovered by conduit 30. The 350° F plus fraction in conduit 30 is further separated to isolate a 350° to 550° F kerosine fraction withdrawn from separator 32 by conduit 34. The remainder of the charge boiling above 550° F and up to about 650° F is withdrawn by conduit 36 from separator 32. This is a low pour point, 550° to 650° F diesel oil product.

According to this invention, the process arrangement comprising the zeolite conversion zone 38 is operated preferably in a blocked out fashion with either the 350° to 550° F kerosine charge in conduit 34 or the heavy 650° F plus distillate in conduit 24 being separately processed in the crystalline zeolite catalytic upgrading zone 38. The zeolite catalyst 40 in zone 38 is NiZSM-5 compounded with an alumina binder and disposed in a fixed catalyst bed 40. Hydrogen in conduit 42 is provided to the reaction zone and the upgrading is carried out at a temperature in the range of 550°–800° F, a pressure in the range of 100–800 psig and a space velocity in the range of 0.5–5 LHSV. The product of the zeolite catalyst upgrading withdrawn by conduit 44 is distilled or separated in zone 46 into light gases withdrawn by conduit 48, either a 350° F minus or a 400° F minus gasoline fraction withdrawn by conduit 50, depending on the product it is desired to maximize and either a low freeze point 350° to 450° F jet fuel or a low pour point 400° F plus diesel oil withdrawn by conduit 52. The jet fuel may have a 550° F end point.

Having thus generally described the invention and specifically described the preferred processing embodiments thereof, it is to be understood that no undue restrictions are to be imposed by reasons thereof except as defined by the following claims:

We claim:

1. A process of producing high quality gasoline and higher boiling products which comprises hydrotreating a wide boiling range aliphatic hydrocarbon fraction comprising oxygenates boiling in the range of about 350° to 850° F;

separating the hydrotreated product to produce a 650° F plus fraction and a 650° F minus fraction, separating said 650° F minus fraction to produce a gasoline boiling fraction and higher boiling light oil fraction, separating said high boiling light oil fraction to produce a kerosine boiling fraction and a higher boiling distillate fraction having a low pour point;

separately converting said kerosine boiling fraction and said 650° F plus fraction with a catalyst comprising a special zeolite component having a silica to alumina ratio of at least 12 and a constraint index of 1 to 12, at a temperature in the range of about 500° to 800° F, and at a space velocity of about 0.5 to 5 WHSV, to produce a conversion product of said zeolite catalyst, separating product obtained by converting said 650° F plus distillate fraction with said special zeolite catalyst to produce a $C_4$ minus gaseous product, a naphtha boiling range product, and a higher boiling distillate product suitable for producing jet fuel boiling range material and diesel fuel; and separating product obtained by converting said kerosine boiling fraction with said special zeolite catalyst to produce a $C_4$ minus gaseous product, a naphtha boiling range product and a kerosine boiling range product suitable for use as jet fuel.

2. The process claimed in claim 1 wherein said zeolite is ZSM-5.

3. The process of claim 1 wherein said gasoline boiling fraction separated from said 650° F minus fraction has an end boiling point within the range of 350° to about 400° F.

4. The process of claim 1 wherein said kerosine boiling fraction separated from said 650° F minus fraction boils up to about 550° F.

5. The process of claim 1 wherein a naphtha boiling product is recovered from said zeolite catalyst conversion operation having an end boiling point within the range of 350° to 400° F.

6. The process of claim 1 wherein a kerosine product of desired low freeze point boiling within the range of 350° to 450° F is recovered from said zeolite catalyst conversion operation.

7. The process of claim 1 wherein a diesel fuel is recovered from said zeolite catalyst conversion operation boiling above 400° F.

8. The process of claim 1 wherein said zeolite conversion catalyst is in admixture with from 0.5 to 5 weight percent of a metal hydrogenation/dehydrogenation component.

9. The process of claim 8 wherein a hydrogen pressure within the range of 100 to 800 psig is employed in said zeolite conversion operation.

* * * * *

UNITED STATES PATENT AND TRADEMARK OFFICE

CERTIFICATE OF CORRECTION

PATENT NO. : 4,044,064

DATED : August 23, 1977

INVENTOR(S) : DONALD MILSTEIN and THOMAS R. STEIN

It is certified that error appears in the above-identified patent and that said Letters Patent are hereby corrected as shown below:

Column 1, line 13 After "where" eliminate -- the --.

Column 1, line 58 "definic" should be -- olefinic --

Column 4, line 46 "500°" should be -- 550° --.

Signed and Sealed this

***Twenty-second* Day of *November 1977***

[SEAL]

*Attest:*

RUTH C. MASON
*Attesting Officer*

LUTRELLE F. PARKER
*Acting Commissioner of Patents and Trademarks*